United States Patent
Sherman et al.

(10) Patent No.: US 10,456,788 B2
(45) Date of Patent: Oct. 29, 2019

(54) APPARATUS FOR DISRUPTION OF CELL AND TISSUE SAMPLES IN MULTI-WELL PLATES

(71) Applicants: Yury Sherman, Roslindale, MA (US); Michael Sherman, Ma'ale Adumim (IL); Ilya Alexandrov, Natick, MA (US); Yehuda Buff, West Roxbury, MA (US)

(72) Inventors: Yury Sherman, Roslindale, MA (US); Michael Sherman, Ma'ale Adumim (IL); Ilya Alexandrov, Natick, MA (US); Yehuda Buff, West Roxbury, MA (US)

(*) Notice: Subject to any disclaimer, the term of this patent is extended or adjusted under 35 U.S.C. 154(b) by 0 days.

(21) Appl. No.: 16/259,766

(22) Filed: Jan. 28, 2019

(65) Prior Publication Data
US 2019/0232295 A1    Aug. 1, 2019

Related U.S. Application Data

(60) Provisional application No. 62/709,674, filed on Jan. 26, 2018.

(51) Int. Cl.
*B01L 9/00* (2006.01)
*B01L 3/00* (2006.01)

(52) U.S. Cl.
CPC .......... *B01L 9/523* (2013.01); *B01L 3/50853* (2013.01); *B01L 2200/025* (2013.01); *B01L 2300/04* (2013.01); *B01L 2300/0816* (2013.01)

(58) Field of Classification Search
CPC .. B01L 9/523; B01L 3/50853; B01L 2300/04; B01L 2200/025; B01L 2300/0816
See application file for complete search history.

(56) References Cited

U.S. PATENT DOCUMENTS

2004/0256963 A1* 12/2004 Affleck ..................... C30B 7/00
                                                                    312/209

* cited by examiner

*Primary Examiner* — Dennis White
(74) *Attorney, Agent, or Firm* — Christopher Mayle; John D. Houvener; Bold IP, PLLC

(57) ABSTRACT

The present invention relates to an apparatus for substantially horizontally oscillating one or more multi-well plates containing a liquid, a solid, or a mixture thereof that operates to thoroughly disrupt solid substances in multi-well plates. The apparatus provides oscillation of plates in a horizontal direction through the use of springs and rotating mechanical components. The apparatus includes a circular rotating ring having a toothed circumference that rotates horizontally, plate holder, and a spring attached to the housing and in constant contact with the plate holder. The apparatus can be used in a cold room or placed in a refrigerator to keep the substances at low temperature and to eliminate noise when the disruptor operates.

9 Claims, 6 Drawing Sheets

APPARATUS FOR DISRUPTION OF CELL AND TISSUE SAMPLES IN MULTI-WELL PLATES

CROSS-REFERENCE TO RELATED APPLICATIONS

This application claims priority to U.S. Provisional Application No. 62/709,674 filed Jan. 26, 2018, which is incorporated by reference in its entirety.

FIELD OF THE DISCLOSURE

The present invention relates generally to an apparatus for effecting physical and chemical changes in samples of materials being tested or processed in a laboratory or production facility.

BACKGROUND

Even with modern technology and advancements with biological devices, it remains relatively difficult to disrupt biological mixtures containing cells, tissues and other liquids that need to be disrupted in a laboratory setting. The most common methods of cell disruption rely on machines that oscillate microtubes. However, these machines are often noisy and disruptive in a lab. Further, they often do not provide efficient controllable oscillation to ensure a desired result is achieved. Additionally, known machines often can not be used in refrigerators or in cold environments, which limits the usefulness of such machines.

Thus, a way to disrupt cell and tissue samples in multi-well cell plates capable of being performed efficiently and in cold environments is need.

The disclosed system and apparatus is directed to overcoming one or more of the problems set forth above.

SUMMARY

The objects of the present invention are accomplished by an apparatus and system for disrupting substances contained in multi-well plates. The apparatus and system having a housing that has a box holder to receive one of said multi-well plates, and the box holder is mounted for reciprocative or oscillatory movement inside the housing. The apparatus and system further having a pair of substantially coextensive guide rod having their respective ends rigidly fastened to spaced apart portions of the housing so as to be immovable therein and a compression spring carried coextensive with a guide rod slider located on said guide rod. In one embodiment, one of said guide rods have an end fixed with respect to said housing and the guide rod slider is fixed with respect to said box holder, so as to normally bias said box holder in a direction away from said fixed end of said spring.

The apparatus and system can further have an electric motor and a ratchet wheel fixedly carried in said housing and turnable by operation of said electric motor. The ratchet wheel can have two cam surfaces at its periphery and a cam surface on said box holder, and the cam surface and box holder are continuously spring biased by said compression spring into engagement with the cam surfaces of the ratchet wheal with one cam surface at a time to reciprocate the box holder against the force of the compression spring as the ratchet wheel is turnably driven by the electric motor. The reciprocative or oscillatory movement of the box plate will result in correspondent of said multi-well plate and disruption of said substances in said wells.

Certain terminology and derivations thereof may be used in the following description for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

BRIEF DESCRIPTION OF THE DRAWINGS

The preceding and following embodiments and descriptions are for illustrative purposes only and are not intended to limit the scope of this disclosure. Other aspects and advantages of this disclosure will become apparent from the following detailed description.

Embodiments of the present disclosure are described in detail below with reference to the following drawings. These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

DETAILED DESCRIPTION

Figure 1:
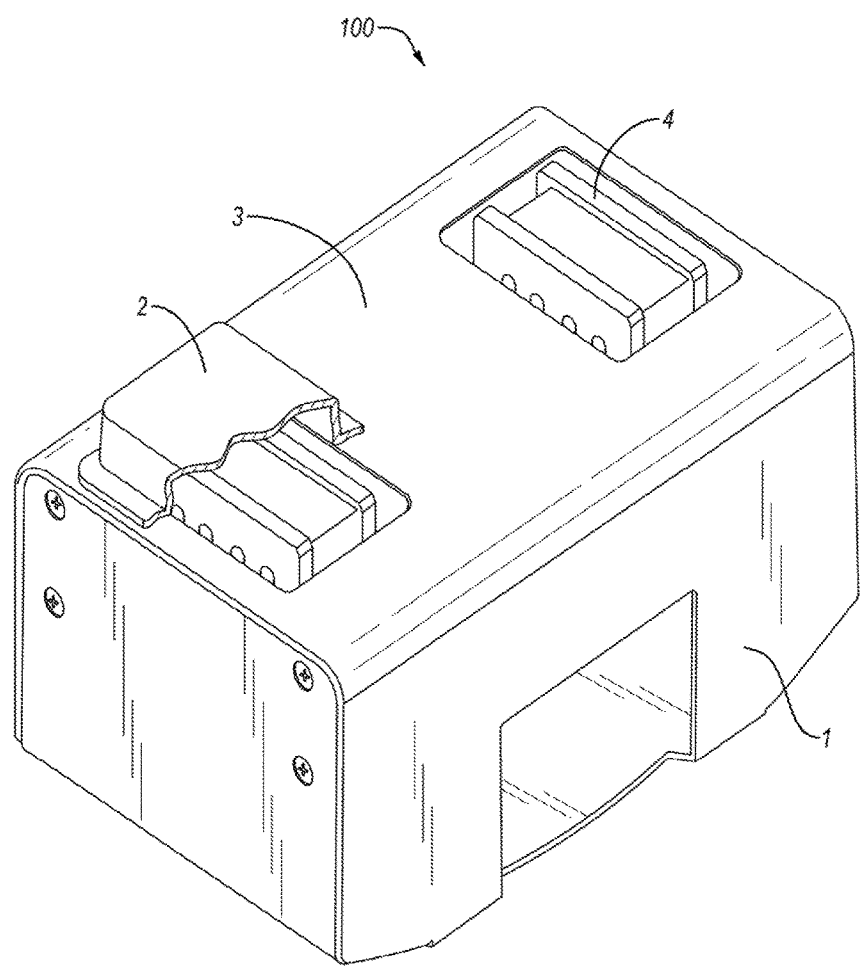
FIG. 1 is a perspective view of an exemplary disruption apparatus according to various aspects of the present disclosure.

In the Summary above and in this Detailed Description, and the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and grammatical equivalents thereof are used herein to mean that other components, ingredients, steps, among others, are optionally present. For example, an article "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Certain terminology and derivations thereof may be used in the following description for convenience in reference only, and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The present description includes one or more embodiments for various disruption apparatus and systems that may be used for disruption of cell and tissue samples inside multi-well plates by oscillating the plates horizontally. In one or more embodiments, a disruption apparatus may or may not include one or more methods for disrupting cell and tissue samples inside multi-well plates. Elements included herein are meant to be illustrative, rather than restrictive. Persons having ordinary skill in the art relevant to the present disclosure may understand there to be equivalent elements that may be substituted with the present disclosure without changing the essential function or operation of the disruption apparatus.

Figure 2:
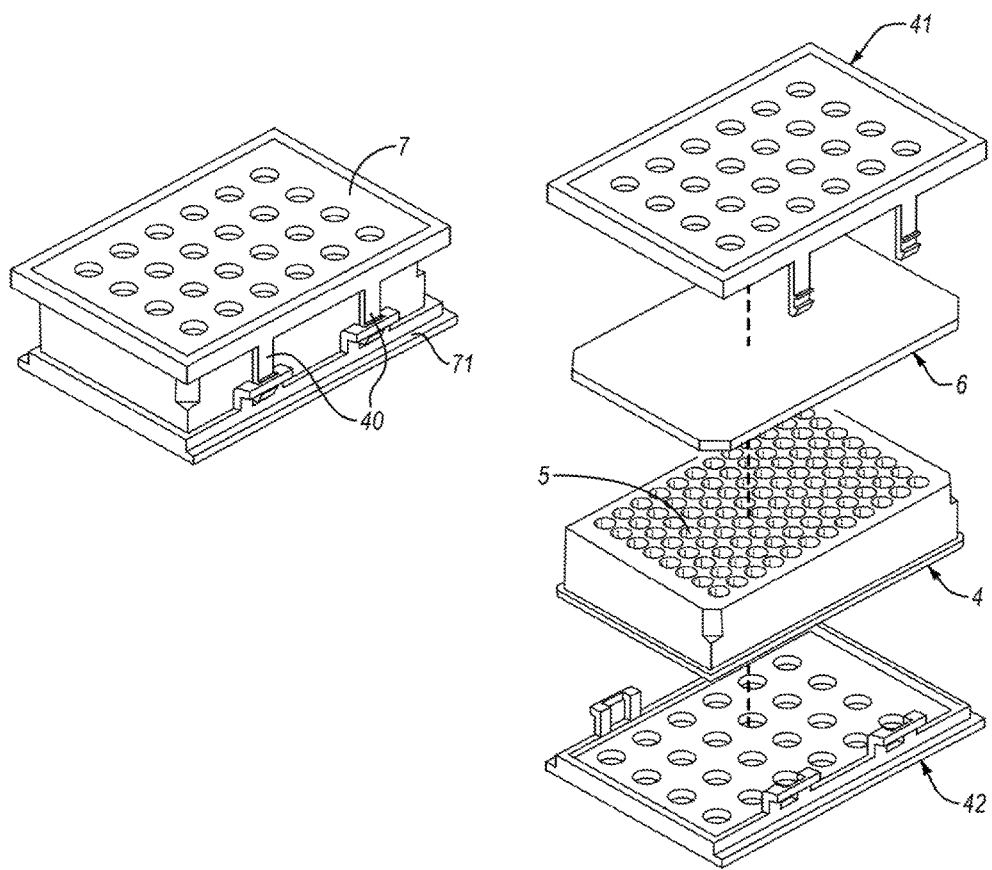
FIG. 2 is an exploded perspective view of the plate of the exemplary disruption apparatus of FIG. 1.

The figures below contain reference numerals, and a listing of reference numerals is as follows:

1 housing
2 removable covers
3 top of housing
4 plate
5 wells/bind holes
6 elastic gasket
7 box
8 box holder
10 electric motor
11 vertical motor axis shaft
12 ring/rachet wheel
13 tooth/teeth
14 formed step
15 wedge
16 guide rod slider
17 compression springs
21 guide rod
22 guide rod stop
23 central holder
32 bushing
40 latches
41 first cover
42 second cover
71 guiding means
81 the ring first end
82 the ring second end
121 toothed circumferences
201 housing
210 electric motor
211 vertical motor axis shaft Turning to FIG. 1 a perspective view of an exemplary disruption apparatus 100 according to various aspects of the present disclosure is shown. The disruptor comprises a housing 1 (FIG. 1) into which one, or preferably two, plates 4 are installed and processed, each plate having a number of wells 5 (as shown in FIG. 2), as an example a total of 96 wells in one embodiment, used in laboratory practice. In another embodiment, any number of wells can be used. In a further embodiment, there can be two different functions of multi-well plates: 1) Tested substances are placed and subjected to disruption directly in wells as described below, and 2) Tested substances are placed and subjected to disruption in small test tubes which are placed in the multiple wells. In this method, the wells can accommodate the tubes, and all other structural specifics of described multi-well plates, including plate holders and mechanism for moving the holders are the same as described below. These embodiments include cells, tissues and other biological substances subjected to disruption in tubes or wells for testing.

Cells or tissues to be disrupted are placed into the wells 5 together with liquid components and beads or particles and are subjected to disruption for various test procedures. At the top of the housing 3 there are removable covers 2, one cover for one plate, closing the plate inside the housing to bar access of the operator's hands to the plate when the apparatus is functioning. In one embodiment, during the disruption process the wells 5 must be water tight and tightly closed with respect to one another. Accidental cross contamination of disrupting media placed in different wells must be carefully avoided.

Such closure is usually achieved by using one sided sticky scotch-like film which closes the mouths of the wells 5 by means of the adhesive character of the sticky film.

FIG. 2 is an exploded perspective view of a plate 4 of the exemplary disruption apparatus of FIG. 1. The left drawing of FIG. 2 shows an assembled plate 4, and the right drawing shows an exploded view of a plate 4. In one embodiment, in order to make the closure fail safe, reliance is placed on a sheet-like gasket 6 of elastic rubber-like material having its sticky face positioned toward the wells prior to assembling the cover, so that there is established a seal of the wells. In operation, the gasket 6 is placed in a box 7 of special construction.

Box 7 comprises two covers, the first cover 41 and the second cover 42. In one embodiment, during use the covers are at open and closed ends of the wells 5, respectively, and there are latches 40 releasably connecting the first and second covers 41 and 42 at the sides of the box 7. In this embodiment, inside the first cover 41, the gasket 6 of elastic rubber-like material faces toward the open ends of the wells 5. The gasket is glued, or fixedly attached by another means, to the first cover 41 such that when the covers are forced toward each other and secured together by latches 40, there is established a reliable closure of the open ends of the wells 5 as needed during the disruption process. This in turn prevents cross contamination of the cells and tissues to be disrupted.

Figure 5:
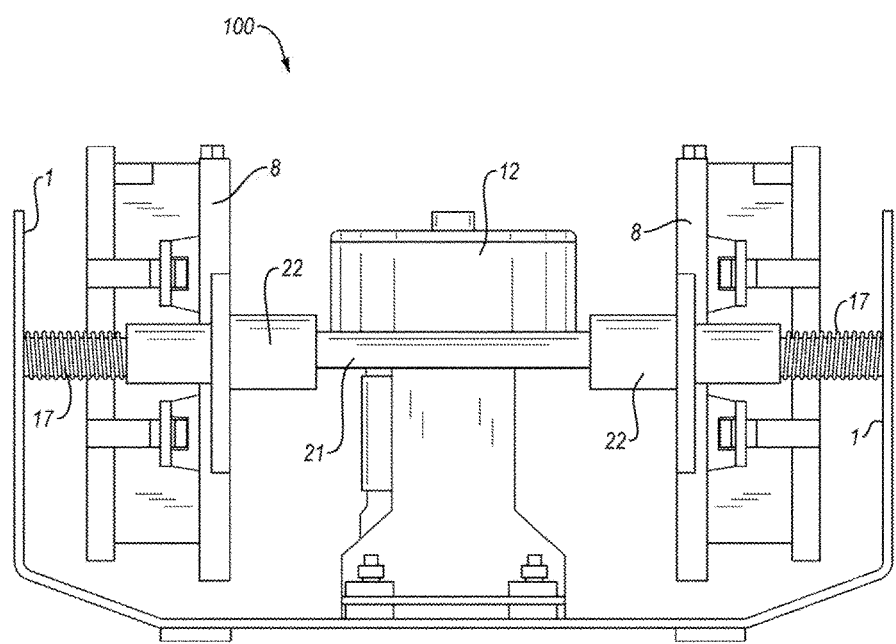
FIG. 5 is a side view of the disruption apparatus of FIG. 1.

In one embodiment during operation, box 7 and the plate 4 it is inserted into are so oriented that—the wells 5 assume a horizontal position. Box 7 also includes a guiding means in the form of a tongue, for easy attachment and removal of the box from a cooperable groove in a box holder 8 (as shown in FIG. 5).

Figure 3:
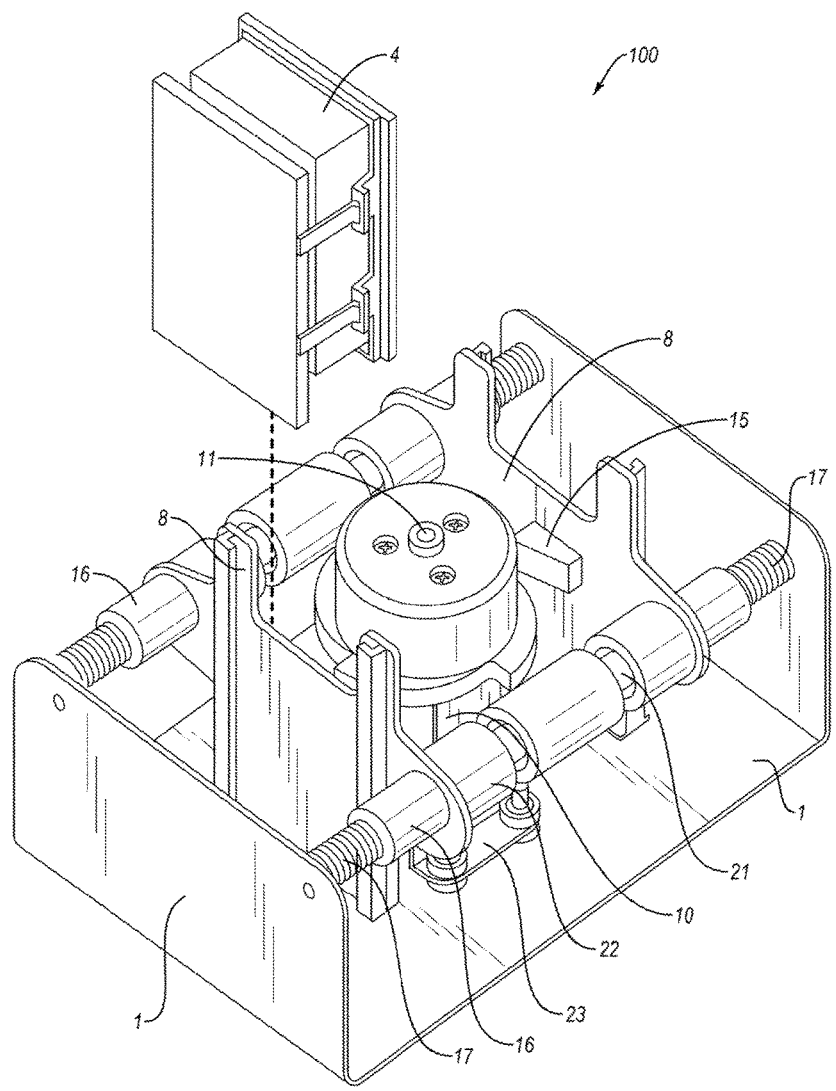
FIG. 3 is a perspective of the disruption apparatus of FIG. 1 with the top cover removed.

FIG. 3 is a perspective of the disruption apparatus of FIG. 1 with the top of the housing 3 removed to show the internal components of the disruption apparatus 100. In this embodiment, the housing 1 also comprises a central holder 23 that has an electric motor 10 located inside, and two box holders 8. The vertical motor axis shaft 11 of the motor rotates a ring 12 having a toothed circumference 121. In one embodiment, the toothed circumference 121 has at least one tooth 13. In a further embodiment, the toothed circumference 121 has 2, 3, 4 or more teeth 13. The number of teeth is variable depending on the design plan and desired oscillations. The ring 12 is rotated substantially horizontally about a vertical motor axis shaft 11. The teeth 13 are of smoothly curved shape, similar to that of a cam ramp.

In one embodiment, between two adjacent teeth 13, the ring first end 81 and the ring second end 82 are spaced a different distance from the axis of rotation of the ring 12. As a result, at the border of two adjacent teeth 13 there is formed a step 14. In this embodiment, each box holder 8 includes a wedge 15 that functions as a cam lug. The cam lugs are engaged by the teeth 13 and steps 14 of the ring which for cam ramps on the ring 15 as it rotates and interacts with the wedge 15. Thus, the surfaces of the wedges 15 provide for smooth sliding of the teeth 13 therearound when the ring 12 is turnably power driven. This sliding causes substantially horizontal forces resulting in periodic opposite displacement of the box holders in directions outward from the rotating ring. Each box holder 8 is supported by two guide rod sliders 16 that are located on a guide rod 21, inside the housing 1 and the resulting movement of each box holder is along the rod 16 in a reciprocating manner as can be readily seen in FIG. 3.

Springs 17, each concentric with the two guide rods 21 respectively, are installed between the housing 1 and in constant contact with the guide rod sliders 16, in this embodiment, are fixed from making any vertical movement but are slideable horizontally along the guide rods 16. In this embodiment, each of the box holders 8 are attached to one or more guide rod sliders 16. Accordingly, the spring forces applied to the holder(s) 8 provide continuous pressure on each plate holder, counteracting the horizontal force applied to each of the two plate holders when the rotating ring turns. These forces cause the oscillations of the plate holders when the rotating ring turns, which in turn cause horizontal oscillation of the plates, and consequent horizontal reciprocating of the wells and their contents.

In one embodiment, a guide rod stop 22 on the guide rod 21 in-between the two box holders 8 can be used. In this embodiment, the stop serves the purpose of allowing the guide rod slider 16 to move past the location of the stop. In a non-limiting embodiment, this is used to control the oscillations of the plates by limiting their horizontal lengths. In a further embodiment, the guide rod stops 22 can be moved along the guide rod 21 to adjust the oscillation lengths, wherein the closer the box holder 8 is to the teeth, the further the teeth can push the box holder away from the ring 12.

In the FIG. 3 view, a three-piece guide rod stop 22 is used, with a central guide rod stop included. In a further embodiment, the guide rod stop 22 is one elongated piece located on the guide rod 21 and in-between the box holders 8.

From the above it can be seen that we have provided a novel and improved disrupter apparatus 100 that is simple in its structural features, and reliable in operation. It is to be noted that the apparatus can operate quietly by installation of the covers, and is capable of operation in a cool environment, such as a laboratory cooling mechanism, or a refrigerator. The disruptor apparatus 100 as described thus constitutes a distinct advance and improvement with respect to existing oscillating systems and constructions heretofore known.

Figure 4:
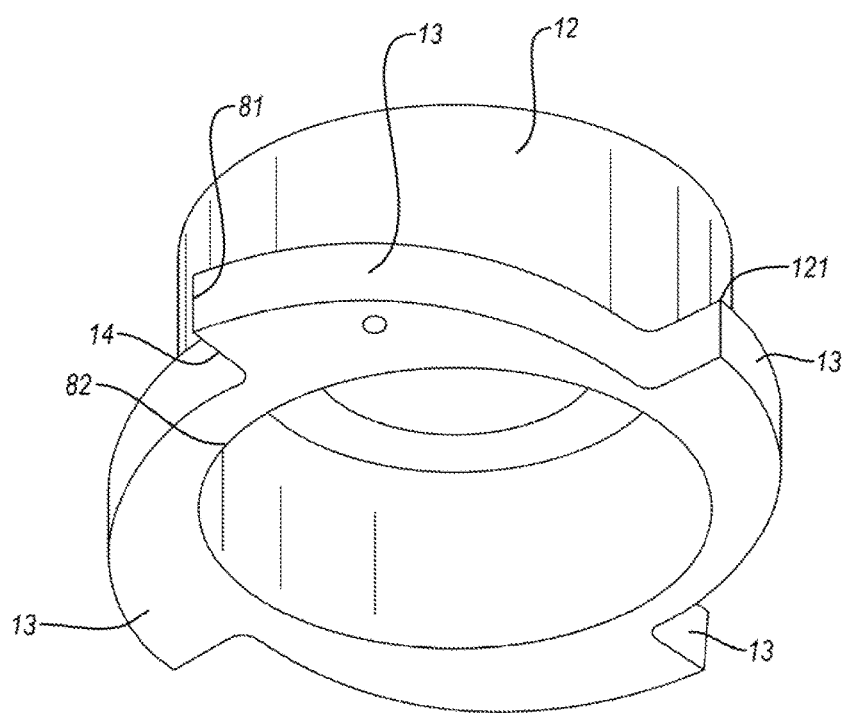
FIG. 4 is a close-up perspective view of a rotating ring with a toothed circumference of the disruption apparatus of FIG. 1.

FIG. 4 is a close-up perspective view of the rotating ring 12 with a toothed circumference of the disruption device 100 of FIG. 1. As show in this figure, is four teeth located on the toothed circumference 121, and the steps 14 located in between adjacent teeth 13.

FIG. 5 is a side view of the disruption device 100 of FIG. 1. This view shows the housing 1, the box holders 8, the ring 12, the guide rod 21, the guide rod slider 16, the guide rod stop 22, and the springs 17. In this embodiment two guide rod stops 22 are located on each guide rod 21.

Figure 6:
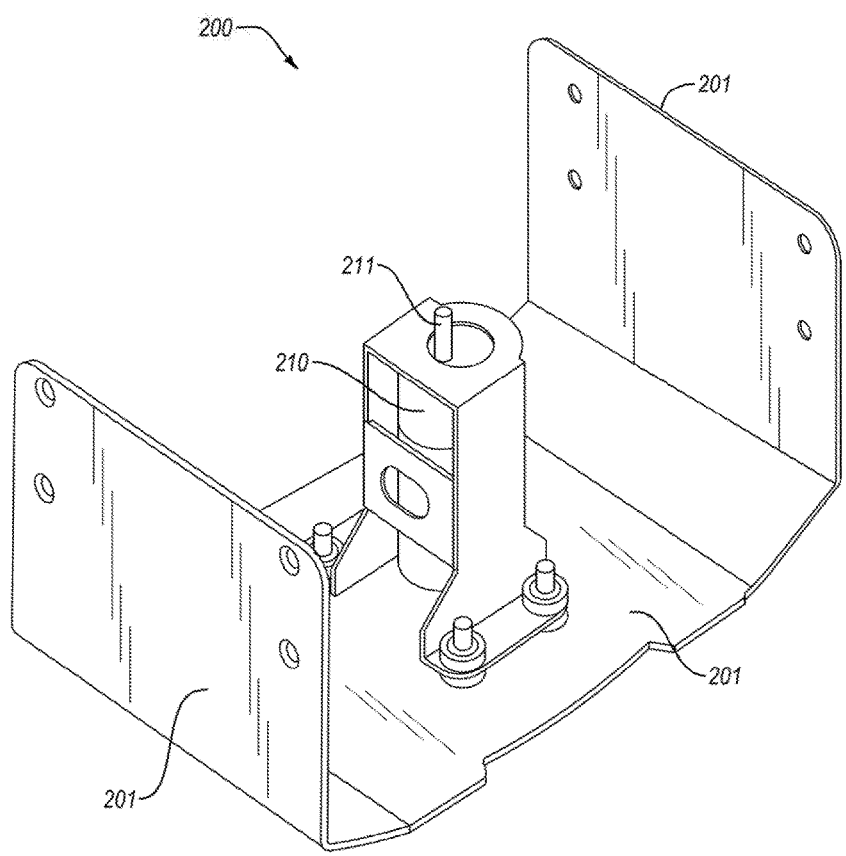
FIG. 6 is a perspective view of an exemplary disruption apparatus according to various aspects of the present disclosure.

FIG. 6 is a perspective view of an exemplary disruption apparatus 200 according to various aspects of the present disclosure. In this embodiment, disruption apparatus 200 has a housing 201, an electric motor 210, and a vertical axis shaft. This embodiment shows the use of a five-surface housing 5. In a non-limiting embodiment, the FIG. 6 embodiment can be adapted to provide a cam that is capable of providing vertical osculation to a plate, as opposed to horizontal oscillation as shown above.

It is noted that any of the disruption apparatus as shown in FIGS. 1-6 may be formed from any suitable material, even if the cross-hatching used in any of these figures may be illustrative of a material.

Advantageously, the present description provides one or more embodiments of various types of disruption apparatuses. Each disruption apparatus depicted herein provides advantages that overcome shortcomings of other types of disruption apparatus that are used conventionally. Further, the various embodiments shown in the figures and described herein accommodate different sized disruption apparatuses and may be used in various applications, including, but not limited, oscillation of cell and tissue samples in multi-well cell plates. It is noted that the various embodiments of disruption apparatuses presented herein may be used in many other ways other than to provide oscillation of cell and tissue sample in multi-well cell plates. For example, the various disruption apparatuses can be used for effecting physical and chemical changes in samples of materials being tested or processed in a laboratory or production facility. Thus, the various embodiments described in the present description include a number of novel and helpful components that provide enhanced apparatuses to benefit a user.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated. The present invention according to one or more embodiments described in the present description may be practiced with modification and alteration within the spirit and scope of the appended claims. Thus, the description is to be regarded as illustrative instead of restrictive of the present invention.

What is claimed is:

1. An apparatus for disrupting substances contained in multi-well plates, said apparatus comprising:
    a housing;
    one or more guide rod attached to said housing;
    one or more box holder attached to one or more guide rod slider, wherein each of said one or more guide rod slider are movably attached to the one or more guide rod;
    one or more compression spring each located on one of said one or more guide rod, wherein each of said one or more compression spring on the guide rod is located in-between said housing and said box holder;
    an electric motor;
    a ring having one or more circumferential tooth, wherein said ring is configured to be spun by said electric motor; and
    at least one wedge located on each of said one or more box holder, wherein said wedge and said one or more box holders configured to being continuously spring biased by said one or more compression springs into engagement with the one or more circumferential tooth.

2. The apparatus of claim 1, further comprising a cooperable means on said one or more box holder and multi-well plates configures to releasably attach to said one or more box holder.

3. The apparatus of claim 1, wherein said one or more box holder further comprises an attachable multi-well plate.

4. The apparatus of claim 3, wherein the multi-well plate further comprises a first cover, a second cover and an elastic gasket.

5. The apparatus of claim 1, wherein said housing further comprises spread apart walled portions that are substantially parallel to one another.

6. The apparatus of claim 1, wherein the ring has four circumferential teeth and in-between said teeth is a step.

7. The apparatus of claim 1, wherein said one or more box holder and an attachable multi-well plate have cooperable tongue and groove formations to enable the multi-well plate to be slidably inserted onto the one or more box holder inside the housing, and to be captive therein for effecting simultaneous reciprocation of the multi-well plate with reciprocation of the box holder.

8. The apparatus of claim 1, wherein said one or more guide rod further comprises a guide rod stop.

9. The apparatus of claim 1, wherein said housing further comprises a central holder, wherein said central holder houses said electric motor.

* * * * *